United States Patent [19]

Forbes

[11] Patent Number: 4,465,937
[45] Date of Patent: Aug. 14, 1984

[54] APPARATUS FOR OPTICALLY SCANNING AN OBJECT

[76] Inventor: James A. Forbes, P.O. Box 854, Doylestown, Pa. 18901

[21] Appl. No.: 313,794

[22] Filed: Oct. 22, 1981

[51] Int. Cl.$^3$ .......................................... G01N 21/86
[52] U.S. Cl. .................................... 250/560; 356/376
[58] Field of Search ........... 250/560, 561, 236, 203 R; 350/6.5; 356/386, 387, 376; 209/535

[56] References Cited

U.S. PATENT DOCUMENTS

| | | | |
|---|---|---|---|
| 3,061,730 | 10/1962 | Jankowitz | 250/203 R |
| 3,328,000 | 6/1967 | Rottmann | 250/223 B |
| 3,615,139 | 10/1971 | Bostrom | 250/236 |
| 3,922,094 | 11/1975 | Colding et al. | 250/560 |
| 4,089,608 | 5/1978 | Hoadley | 356/376 |
| 4,120,403 | 10/1978 | Stephanos | 250/560 |
| 4,297,034 | 10/1981 | Ito et al. | 356/376 |
| 4,358,202 | 11/1982 | Puffer et al. | 250/236 |

OTHER PUBLICATIONS

Brochure, "CCD133/143 1024/2048-Element High-Speed Linear Image Sensor, Fairchild Charge-Coupled Device", Fairchild Camera and Instrument Corporation, Mountain View, California (1979).
Brochure, "Computer Controlled Camera System", Cynosure Corporation, Holicong, Pennsylvania.

*Primary Examiner*—David C. Nelms
*Assistant Examiner*—J. Brophy
*Attorney, Agent, or Firm*—Lane, Aitken & Kananen

[57] ABSTRACT

An optical scanning apparatus includes a light source for directing light energy through an object scanning zone toward and to a photo responsive array having a plurality of linearly arranged photo detectors that provide an electrical output in response to light energy thereon. The electrical output of the photo responsive array is representative of the exterior dimensions of the scanned object. The light source is mounted in a scanning head that is rotated about the object and advanced relative to the length of the object to enable scanning of the entire peripheral surface of the object. The invention is suitable for scanning the peripheral surface of both an object having a discrete axial length as well as an object having an indeterminate length.

12 Claims, 6 Drawing Figures

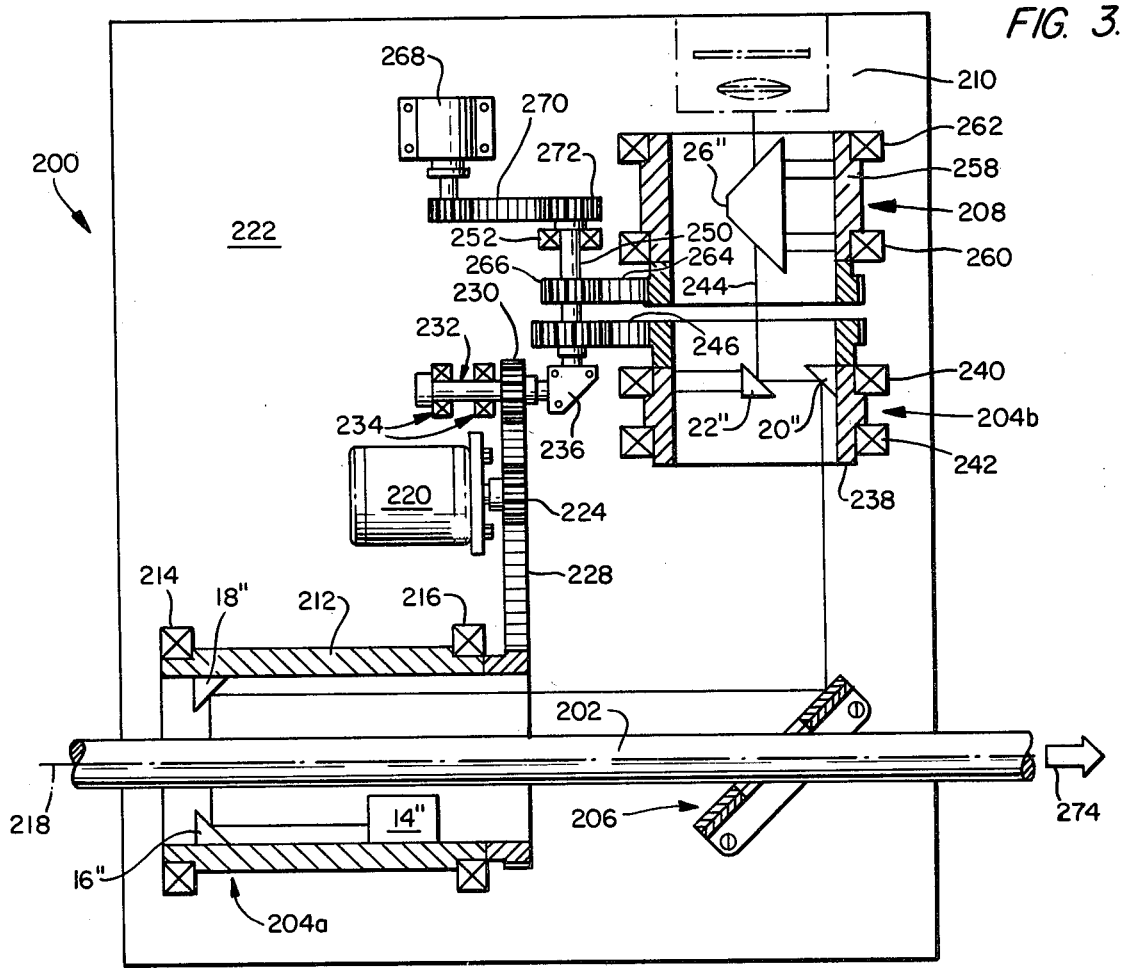
FIG. 3.
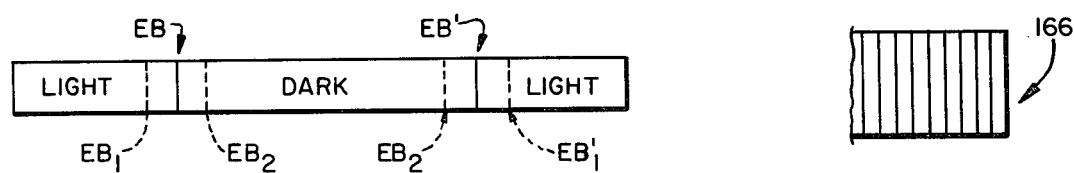
FIG. 4.
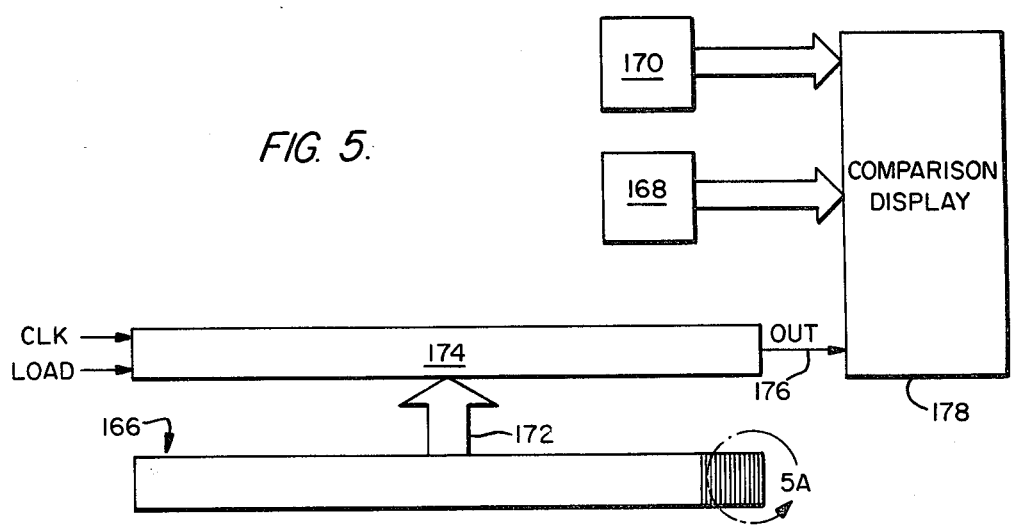
FIG. 5A.
FIG. 5.

APPARATUS FOR OPTICALLY SCANNING AN OBJECT

BACKGROUND OF THE INVENTION

The present invention relates to a method and apparatus for optically scanning objects and, more specifically, to optically scanning the peripheral surface along the entire longitudinal length of an object of either discrete or indeterminate length to obtain dimension related information.

In many manufacturing operations, the object manufactured must conform to specific dimensional limits including, for example, outside diameter, overall length and/or contour dimensions. In the past, manufacturing operations have measured the manufactured objects using appropriate tools, such as micrometers, vernier calipers, and go/no-go gauges to determine if the manufactured object conformed to the required dimensional specifications. Other measurement techniques have included optical comparators in which the profile of the object was projected onto a screen provided with appropriate dimension indicia. While the aforementioned measuring techniques and devices are generally satisfactory, they usually require a human operator and, accordingly, are prone to error and are not suited to high speed automatic manufacturing operations. Additionally, the aforedescribed measuring techniques and apparatus are not suitable in those cases in which the manufactured object must not be touched, for example, in the manufacture of sterilized pharmaceuticals and the like.

SUMMARY OF THE INVENTION

In view of the above, it is a primary object of the present invention, among others, to provide an optical scanning apparatus and method for scanning the peripheral surface of an object to obtain dimension indicative information.

It is also another object of the present invention to provide a method and apparatus for optically scanning an object having both a peripheral surface dimension and a longitudinal dimension.

It is also a further object of the present invention to provide a method and apparatus for optically scanning an object which is consistent with automatic manufacturing techniques.

In accordance with these objects, and others, the present invention provides an apparatus and method for effecting optical scanning of the peripheral surface of an object along the length dimension of the object by directing scanning light from a light source through an object scanning zone to a photo detector array that includes a multiplicity of linearly arranged photo detectors that each provide a signal output in response to light incident thereon. An object to be scanned is supported between the light source and the photo detector array to block or occlude a portion of the scanning light so that the unblocked light will irradiate the photo detectors and provide an electrical signal that is representative of the width of the object being scanned. The light source is mounted in a scanning head which is rotatable relative to the object being scanned and movable relative the length dimension thereof so that the peripheral surface of the object along its entire length can be scanned.

The inventive method and apparatus advantageously permits a rapid and complete scanning of the peripheral surface of an object along its entire length dimension and is well suited to automatic manufacturing operations including those operations in which the manufactured object can not be touched.

BRIEF DESCRIPTION OF THE DRAWINGS

The above description as well as further objects, features, and advantages of the present invention will be more fully understood by reference to the following description of presently preferred but nonetheless illustrative embodiments when taken in connection with the accompanying drawings wherein:

FIG. 3 is a front elevational view of a second embodiment of a scanning apparatus in accordance with the present invention utilizing the optical elements shown in FIG. 1 and in which selected structure has been shown in cross section or omitted for reasons of clarity;

FIG. 4 is an illustration of an exemplary object occluded image obtained with the embodiments of FIGS. 2 or 3;

FIG. 5 is a schematic block diagram of an image sensor and related functional blocks for providing and processing an image derived output signal; and FIG. 5A is an enlarged view of the detailed portion of FIG. 5 taken along lines 5A—5A of FIG. 5.

DESCRIPTION OF THE PREFERRED EMBODIMENT

Figure 1:
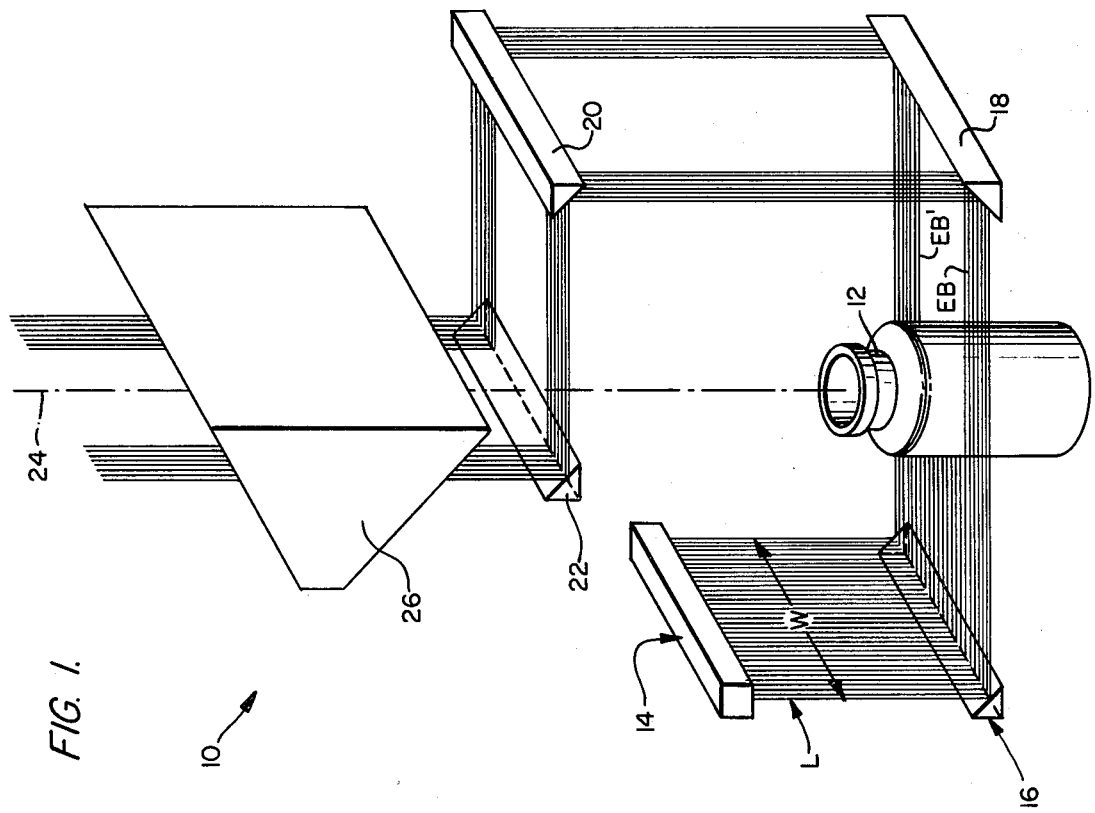
FIG. 1 is a perspective view of the primary optical elements that constitute the optical scanning apparatus of the present invention with various structural features deleted for reasons of clarity.

An optical scanning apparatus in accordance with the present invention utilizes the optical scanning system shown in FIG. 1 and is referred to therein by the reference character 10. In FIG. 1, the various supporting structures for the optical components are not shown for reasons of clarity but are discussed below in relationship to FIGS. 2 and 3. The optical scanning system 10 of FIG. 1 is utilized for scanning the peripheral surface of an object 12, such as an exemplary pharmaceutical vial, to obtain an electrical output signal that is representative of the exterior surface dimensions of the object 12 and which can be used to determine whether or not the object conforms to predetermined manufacturing specifications.

The optical system 10 shown in FIG. 1 includes a light source 14 that provides a relatively wide beam of directed light L having a width dimension W that is wider than the width of the object being scanned. The light is directed from the light source 14 to a first right angle reflector 16, such as a right angle prism or a mirror, having a width sufficient to accommodate the light L from the light source 14. The light reflected by the reflector 16 is directed laterally through an object scanning zone to a second right angle reflector 18. The object 12 to be scanned is supported, as described in more detail below, in the object scanning zone between the reflectors 16 and 18 so that it blocks or occludes a portion of the light rays directed from the light source 14 through the object scanning zone. The light rays reaching the second right angle reflector device 18 represent that portion of the light that is not blocked by the object 12 being scanned and includes two light-todark edge boundaries EB and EB' that optically represent the side boundaries of the object being scanned. The object occluded light is redirected by the second right angle reflector 18 to a third right angle reflector 20 and then a fourth right angle reflector 22 so that the object occluded light is then directed along an axis coincidence with the system axis 24 through a Dove prism 26 (also known as a Delaborne prism) that directs the object occluded light onto an electrical image detector (not shown in FIG. 1) that provides an electrical output signal which includes electrical representations of the light-to-dark edge boundaries EB and EB'. As explained more fully below, the light rays L from the light source 14 can be rotated about the object 12 being scanned so that the entire peripheral surface of an object for any particular plane can be scanned, and, additionally, the light rays L can be caused to move axially along the axis 24 of the system to thereby scan the peripheral surface of the object along its entire length. The corresponding electrical output signals represent the peripheral dimensions of the object about its periphery and along its entire length.

Figure 2:
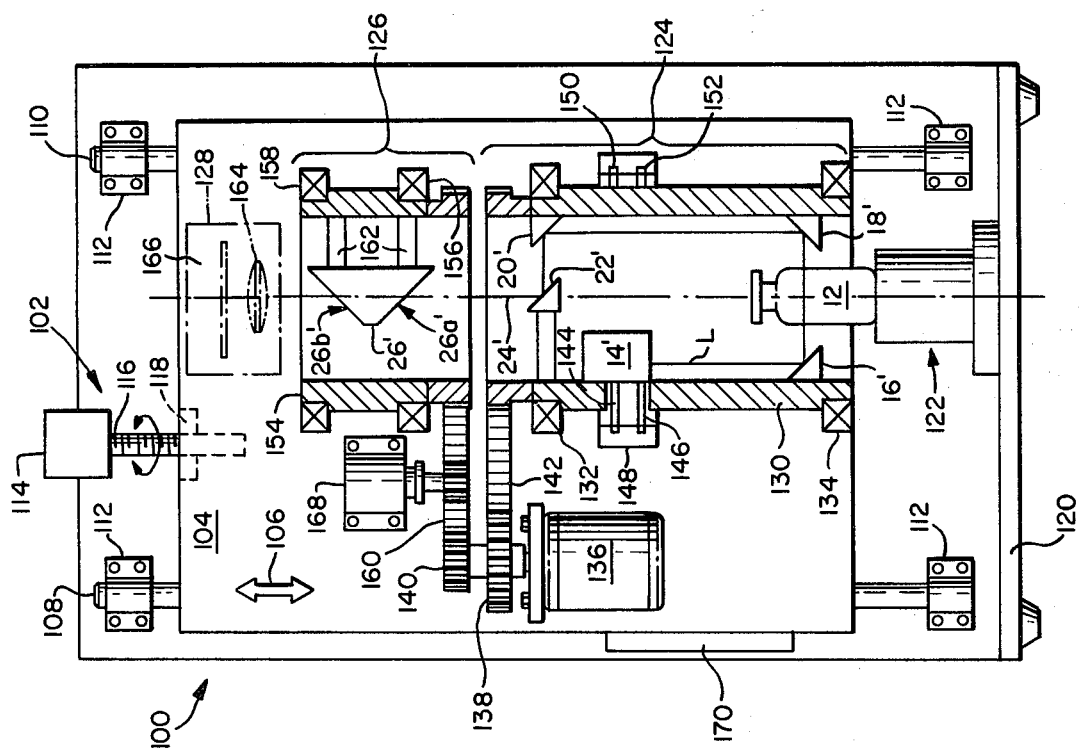
FIG. 2 is a front elevational view of a first embodiment of a scanning apparatus utilizing the optical elements of FIG. 1 in which selected structure has been shown in cross section or omitted for reasons of clarity.

A first embodiment of an object scanning apparatus that incorporates the optical system 10 of FIG. 1 is shown in FIG. 2 and is generally referred to therein by the reference character 100. The optical scanning apparatus 100 includes a vertically aligned frame 102 that supports a component mounting plate 104 for guided bidirectional movement relative the frame 102 in the vertical direction as indicated by the double arrow 106. While various arrangements for effecting the guided vertical movement of the support plate 104 are suitable, the arrangement of FIG. 2 is preferred and includes first and second cylindrical guide bars 108 and 110 (shown extending from above and below the support plate 104) secured at their respective ends to the frame 102 by brackets or clamps 112. The support plate 104 is coupled to its guide bars 108 and 110 by cylindrical sleeve bearings (not specifically shown) that are secured to the support plate 104 and encircle or embrace the guide bars 108 and 110 with a sliding fit therebetween so that the support plate 104 can be moved bidirectionally in the vertical direction. Guided movement in the vertical direction is effected through a drive motor 114 secured to the frame 102. The motor 114 is connected to and adapted to drive a threaded lead screw 116 which, in turn, is in threaded engagement with a nut 118 (shown in broken line illustration) secured to the support plate 104 so that rotation of the lead screw 116 in one direction or the other will cause corresponding upward or downward movement of the support plate 104 relative to the frame 102.

A horizontal shelf or base 120 extends from the lower edge of the frame 102 and has an object supporting platform or base 122 mounted thereon. As shown in FIG. 2, an object 12 to be scanned, such as the pharmaceutical vial, is positioned atop the object support base 122 in the object scanning zone located thereabove.

The scanning system for scanning an object 12 in the object scanning zone includes an object scanning head 124, a scanned image transfer head 126, and an image processing unit 128.

The object scanning head 124 includes a hollow, cylindrical drum 130 (shown in cross section in FIG. 2) having an inside diameter and a length dimension sufficient to accommodate the object 12 being scanned and the related optical elements described below. The drum 130 is mounted in appropriately sized and supported anti-friction bearings 132 and 134 for rotation in a preferred direction (e.g., clockwise) about the vertical system axis 24'. A drive motor 136 is secured to the support plate 104 adjacent the drum 130 and is provided with an output shaft (not shown) that has two adjacent toothed sprockets 138 and 140 secured thereto. A cogged or toothed drive belt 142 is entrained about the first sprocket 138 and about the upper end of the drum 130, which is provided with complementary teeth for engaging the cogged belt 142. Operation of the motor 136 in response to the application of power from a suitable power source causes rotation of the drum 130 in its bearings 132 and 134 about the axis 24'.

A light source 14' is mounted on the interior wall surface of the drum 130 for directing light to the object scanning zone. The light source 14' receives its operating power through a brush/slip ring arrangement that includes two brushes 144 and 146, fabricated from a resilient conductive material such as phosphor bronze, that extend through and are insulated from the wall of the drum 130 and a stationary slip ring assembly 148 that is formed from an annular ring supported circumjacent the outside diameter of the drum 130 and which carries two parallel conductor tracks or rings 150 and 152. The slip rings 150 and 152 are connected to a source of power through appropriate cables (not shown). The resilient brushes 144 and 146 contact the corresponding slip rings 150 and 152 as the drum 130 rotates so that power is effectively transmitted to the light source 14'.

Light energy is directed from the energized light source 14' to the first right angle reflector 16' which is secured to the interior wall of the drum 130 adjacent to the object to be scanned. The reflector 16' directs the light through the object scanning zone to the second right angle reflector 18'. The light that reaches the second right angle reflector 18', which light includes edge boundaries defined by the edges of the object being scanned as described above in relationship to FIG. 1, is reflected by the third right angle reflector 20' and the fourth right angle reflector 22' along the system axis 24' as described above in connection with FIG. 1. When the object scanning head 124 is rotated during an object scan, the image directed along the axis 24' from the fourth right angle reflector 22' is an image of the object occluded light rotating about the axis 24' at a speed of rotation equal to the speed of rotation of the object scanning drum 124.

The image transfer head 126 includes a hollow cylindrical drum 154 (shown in cross section) approximately the same diameter as the object scanning drum 130 and mounted in appropriately sized and supported anti-friction bearings 156 and 158 for rotation about the system axis 24'. A cogged or toothed belt 160 is entrained about the second sprocket 140 of the drive motor 136 and the lower end of the image transfer drum 154. The diameters of the image transfer drum 154, the object scanning drum 130, and the first and second drive sprockets 138 and 140 are selected so that the image transfer drum 154 will rotate at one-half the rotational speed of the object scanning drum 130. A Dove prism 26' is positioned in the image transfer drum 154 by suitable supports 162 so that the optical axis of the prism 26' is aligned along the system axis 24'.

The image processing unit 128 is mounted above the image transfer head 126 on the system axis 24' and includes imaging optics, represented by the lens 164 (broken line illustration) for directing the scanned image to a photo detector array 166, described in more detail below, which provides an electrical output in response to the scanned image.

A position determining device, such as a shaft encoder, is coupled to he optical system so that an angular position signal can be obtained representative of the particular angle of the optical system relative to the object 12 being scanned. In FIG. 2, an optical shaft encoder 168 is mounted on the support plate 104 and has an input shaft and cogged wheel (un-numbered) that engages the drive belt 160 that drives the image transfer head 126. Since the optical scanning head 124 and the image transfer head 126 are mechanically coupled through the aforedescribed belt drive system, the electrical output of the shaft encoder 168 will be representative of the rotary position of the optical scanning system relative to the object 12 being scanned. In a similar manner, a linear position encoder 170 is connected between the veritcally movable support plate 104 and the relatively stationary frame 102 and provides an output signal representative of the vertical position of the support plate 104 relative to the frame 102. In practice, the shaft encoder 168 and the linerar position encoder 170 provide an output signal in multi-bit parallel format that defines the measured positions.

In operation, an object 12 to be scanned, such as the illustrated pharmaceutical vial, is placed on the object support base 122 in the object scanning zone between the first and second right angle reflectors 16' and 18'. The drive unit 114 is operated to move the support plate 104 to a preferred initial position, for example, to the upper end of the object 12 being scanned. The light source 14' is operated so that light is directed across the object scanning zone between the first and second right angle reflectors 16' and 18'. The motor 136 is actuated to cause rotation of the optical scanning head 124 at a selected RPM, for example, $K_{RPM}$, and corresponding rotation of the image transfer head at one-half $K_{RPM}$ (by virtue of the relative diameters of the toothed sprockets 138 and 140) and the drive unit 114 is energized to cause the support plate 104 to move downwardly on its guide bars 108 and 110 relative to the support frame 102.

As the support frame 104 and the optical scanning head 124 move, the object 12 will interrupt or block a portion of the light between the first and second right angle reflectors 16' and 18' so that the image arriving at the second right angle reflector 18' will include two spaced apart bands of light interrupted by an intermediate band of darkness, the width of which will be defined by edge boundaries EB and EB' that are a function of the width of the object being scanned as shown in FIG. 4. As the object scanning head 124 rotates about the periphery of the object 12 being scanned, the edge boundaries EB and EB' will change by moving away from each other to reflect a widening of the object being scanned ($EB_1$ and $EB_{1'}$,) or move closer to one another to reflect any narrowing of the object being scanned ($EB_2$ and $EB_{2'}$,). Additionally, the dark band defined between the edge boundaries EB and EB' can shift to the right or left to reflect an eccentric mounting of the object being scanned relative to the system axis 24'. Thus, any object 12 having a width dimension will provide an image representative thereof, and, as the object scanning head 126 is rotated, the resultant image pattern will represent the width of the object 12 for each angular position of the optical scanning head 124 (with the necessary angular information provided by the aforedescribed shaft encoder 168) for any particular vertical position of the object being scanned (with the necessary vertical position information provided by the position encoder170). As the position of the object scanning head 124 is varied along the vertical axis in response to operation of the drive motor 114, the image pattern will also be representative of the width dimension of the object being scanned for the entire exterior surface of the object.

The image pattern obtained during rotation of the optical scanning head 124 and the aforedescribed vertical movement relative the object 12 is directed by the second, third and fourth right angle reflectors 18', 20', and 22' along the system axis 24' into the image transfer head 126. The rotating image pattern from the fourth right angle reflector 22' is directed along the system axis 24' to the entry face 26a' of the Dove prism 26' and is passed through the prism to the exit face 26b' to the image processing unit 128. As is known in the art, the Dove prism 26' provides a continuous rotation of a field through any deviation. As the prism 26' is rotated about an axis parallel to its reflecting face and lying in a plane perpendicular to its refracting faces, the image is rotated at twice the prism rotation angle. Thus, by rotating the scanned image transfer drum 154 at one-half the RPM of the optical scanning drum 130, a stationary scanned-image pattern is presented to the image processing unit 128.

The scanned image is passed through the processing unit optics 164 and imaged onto the photo detector array 166 that includes a multiplicity of contiguous linearly aligned discrete photo detectors, each of which provides an electrical output, such as a voltage output, in response to the incident light thereon. Since the object occluded image will consist of light that is substantially at full brightness (that is, the scanning light that is not blocked by the object) and relative darkness (representing that portion of the scanning light that is blocked by the object), the signal output of the individual photo detectors can assume one of two signal levels and, accordingly, is of a binary nature.

A schematic block diagram of the image processing unit 128 is shown in FIGS. 5 and 5A and includes the photo detector arrary 166 which, as shown in FIG. 5A, includes a plurality of discrete photo detectors. The number of discrete photo detectors may be varied as desired although an array length of several thousand discrete photo detectors is preferred to provide a high level of image resolution. The outputs of the individual photo detectors are connected through a multi-line output buss 172 to the corresponding parallel load inputs of a shift register 174 having sufficient positions to accommodate the multi-bit "word" output of the photo detector array 166. The multi-bit image word is loaded into the shift register 174 by an appropriate 'LOAD' signal applied to the load input of the shift register 174 and the so-loaded word can be serially shifted out of the shift register along an output line 176 to an image information utilizing unit 178. Suitable integrated photo detector array and combined shift registers are manufactured by the Fairchild Camera and Instrument Corporation of Mountain View, Calif. 94042 under part designations CCD 133 (1024 elements) and CCD 143 (2048 elements). The output of the shaft encoder 168 which provides rotary angle information of the optical system and the linear position encoder 170, both outputs of which may be multi-bit parallel signal outputs, are likewise presented to the image information utilizing unit 178. The image information utilizing unit 178 embodies sensor signal conditioning systems, a microcomputer, and the input/output channels necessary to accomplish a variety of tasks. These tasks would typically include comparing the scanned parts against internally stored standards, communicating the results of the comparison to operating persons via indicators, or display panels, and providing the necessary signals for rejecting out-of-tolerance parts.

A second embodiment of an object scanning apparatus is shown in FIG. 3 and referred to generally therein by the reference character 200. In contrast to the object scanning apparatus 100, the object scanning apparatus 200 is designed to scan objects having an indeterminate length such as the illustrated bar 202 and includes a two-part optical scanning head 204a and 204b, an imaging mirror 206, an image transfer head 208, and an image processing unit 210.

The object scanning head 204a is fabricated from a hollow cylindrical drum 212 having an inside diameter and a length sufficient to accommodate the object being scanned and related optical elements. The drum 212 is mounted in appropriately sized and supported anti-friction bearings 214 and 216 for rotation about the longitudinal axis 218 of the object being scanned. A drive motor 220 is secured to a support plate 222 adjacent the drum 212 and is provided with an output shaft (not specifically shown) that has a toothed sprocket 224 secured thereto. A cogged or toothed belt 228 is entrained about the toothed sprocket 224, about one end of the drum 212, and about another toothed sprocket 230 secured to an intermediate drive shaft 232. The intermediate drive shaft 232 is supported in appropriate bearings 234 and is connected to a right angle gear drive 236.

A light source 14" is located on the interior wall surface of the drum 212 for directing light to a first right angle reflector 16" which directs the scanning light across an object scanning zone to a second right angle reflector 18" which in turn directs the object occluded light to the intermediate mirror 206. As shown in FIG. 3, the intermediate mirror 206 is apertured to provide a passage for the bar 202 being scanned and is positioned at an angle to direct the object occluded light from the second image reflector 18" into the image scanning head 204b. The scanning head 204b is fabricated from a hollow cylindrical drum 238 which is sized to accommodate the third and fourth right angle reflector 20" and 22" is mounted in appropriately sized and supported anti-friction bearings 240 and 242 for rotation about an axis 244. The upper end of the drum 238 is provided with toothed formations for engaging a drive belt 246 which is also entrained about a cogged wheel 248. The cogged wheel 248 is mounted on an intermediate drive shaft 250 which is connected at one end to the right angle drive 236 and at the other end to a support bearing 252.

The image transfer head 208 is fabricated from an appropriately sized drum 258 that is mounted in appropriately sized and supported bearings 260 and 262. The lower end of the drum 258 includes toothed formations and has a drive belt 264 entrained thereabout and about a cogged wheel 266 that is mounted on the intermediate drive shaft 250. A shaft encoder 268, similar or identical to the shaft encoder 168 employed in the first embodiment 100, is connected to the intermediate shaft 250 through a cogged belt 270 and a cogged wheel 272 connected to the intermediate shaft 250. A Dove prism 26" is supported within the drum 258 by suitable supports for receiving light energy from the fourth right angle reflector 22" in the scanning head 204b.

Upon energization of the motor 220, the object scanning drums 204a and 204b are caused to rotate simultaneously at the same rotational speed, while the image transfer drum 208 is caused to rotate at one-half the speed of the object scanning heads. Light energy is directed from the light source 14" (which receives its power from a slip ring/brush arrangement similar to that described above in connection with FIG. 2) to the first right angle reflector 16" and across the object scanning zone to the second right angle reflector 18". The object occluded image is thereafter directed to the intermediate mirror 206. As the object scanning head 204a rotates, the object occluded image will orbit or revolve about the object on the reflecting mirror 206 and be reflected to the third right angle reflector 20". As can be appreciated, for a selected portion of the rotation of the object scanning head 204a, the image will be cut-off from the third right angle reflector 20" by the object being scanned. However, for objects that have an essentially cylindrical shape, a minimum scan of 180° will provide a valid scan. The third right angle reflector 20" transfers the image to the fourth right angle reflector 22" which in turn directs the image to the Dove prism 26" rotating at one-half the rotation rate of the optical scanning heads 204a and 204b. Accordingly and as described above in connection with the first embodiment 100, a stationary object occluded image will be presented to the image processing unit 210 which has a structure essentially identical to that described in connection with the first embodiment 100. In contrast to the first embodiment, the optical scanning head 204a merely rotates about the object being scanned with the object scanned being moved longitudinally through the object scanning zone (as indicated by the arrow 274 in FIG. 3) rather than having the object scanning heads moved longitudinally. A position responsive encoder (not shown) may be provided to measure the relative position of the object being scanned as it passes through the object scanning zone.

The object scanning apparatus of the present invention provides a method and apparatus for rapidly and efficiently scanning the peripheral surface of an object along its entire length to provide dimension related information for measuring the object being scanned and is particularly suited to measuring objects that can not be measured by conventional techniques such as sterilized pharmaceutical vials.

As can be appreciated by those skilled in the art, various changes and modifications may be made to the disclosed embodiment of the optical scanning apparatus and method without departing from the spirit and scope of the invention as recited in the appended claims and their legal equivalent.

What is claimed is:

1. An apparatus for optically scanning at least the peripheral surface of an object comprising:
 light generating means for generating light energy for optically scanning the object;
 a hollow scanning head mounted for rotation about a system axis;
 support means for supporting an object to be scanned within said scanning head;
 optical means mounted in said scanning head for directing the light energy toward the object to be scanned including towards at least one edge of the object to be scanned so that the object will occlude a portion of the light, and for directing the object occluded light along the axis;

transfer head means, including a transfer head, mounted for rotation about said axis and having a Dove prism supported therein along said axis for receiving the object occluded light directed from said optical means and for directing said object occluded light along said axis;

light receiving means positioned to receive the light directed from said Dove prism, said light receiving means including a multiplicity of light-responsive elements, each element providing an electrical output representative of the light falling thereon; and drive means coupled to said scanning head and transfer head means for causing rotation of said scanning head and transfer head about the axis, said transfer head being rotated at one-half the rotational speed of said scanning head.

2. The apparatus claimed in claim 1 wherein said optical means further comprises:

a light source for directing light towards the object to be scanned whereby the object to be scanned occludes a portion of the light, and reflecting means for redirecting the object occluded light along the system axis.

3. The apparatus claimed in claim 1 wherein said drive means further comprises:

means for causing relative movement between the object scanning head and the object to be scanned along a longitudinal axis of said object.

4. The apparatus claimed in claim 1 wherein said scanning head further comprises:

a hollow cylinder having a light source mounted on the interior wall thereof for directing light energy toward the object to be scanned and reflector means for redirecting object occluded light along the axis.

5. The apparatus claimed in claim 4 wherein:

said light source receives its operating electrical power from a slip ring/brush combination.

6. The apparatus claimed in claim 4 wherein said scanning head further comprises:

a first right angle reflecting device for receiving light energy directed from said light source and redirecting that light across the inside of the scanning head, second right angle light reflecting means for receiving object occluded light and directing that light along another axis parallel to said system axis, third right angle reflecting means for receiving the light reflected from the second right angle reflecting means and directing that light to a fourth light angle reflecting means which directs the light along the system axis.

7. The apparatus claimed in claim 1 further comprising:

first encoder means connected to said optical means for determining the rotary position of said scanning head relative to the object being scanned.

8. The apparatus claimed in claim 3 further comprising:

second encoder means coupled to said means for causing relative movement for determining the relative position of the optical scanning head relative to the longitudinal axis of the object being scanned.

9. An apparatus for optically scanning the peripheral surface of an object of indeterminate length, said apparatus comprising:

a source of light for providing light energy for optically scanning the peripheral surface of the object;

a first scanning head mounted for rotation about a first axis;

means for supporting an object of indeterminate length along said first axis and for advancing said object along said first axis;

light directing means within said first scanning head for directing the light energy toward said object so that at least a portion of the light energy is blocked by the object;

first reflecting means within said first scanning head for receiving the light energy from said light directing means and for reflecting that light energy in a direction parallel to said first axis;

second reflecting means positioned on said first axis at an angle thereto, said second reflecting means having an opening formed therein through which the object extends, said second reflecting means redirecting the light energy from said first reflecting means at an angle thereto;

a second scanning head mounted for rotation about a second axis and having a third reflecting means mounted therein for receiving the light energy reflected from said second reflecting means;

said third reflecting means redirecting the light energy from said second reflecting means along said second axis;

an optical transfer head mounted for rotation about said second axis and having a Dove prism mounted therein for receiving the light from said third reflector means and directing the light therefrom along said second axis;

photo-responsive means positioned along said second axis to receive the light from said Dove prism, said photo-responsive means providing an electrical output responsive to the light received thereby; and drive means coupled to said first and second scanning heads and said optical transfer head for rotating said first and second scanning heads at a first speed and for rotating said optical transfer head at a speed one-half that of said first measuring speed.

10. The apparatus claimed in claim 9 further comprising:

an encoder means coupled to at least one of said scanning heads for providing an output signal representative of the relative angular position of said at least one scanning head and the object being scanned.

11. The apparatus claimed in claim 9 wherein said light directing means provides a beam of light having a width greater than that of the object being scanned.

12. The apparatus claimed in claim 9 wherein said photo-responsive means further comprises:

a plurality of linearly arranged light responsive elements, each of said elements providing an electrical output in response to light energy received thereby.

* * * * *